United States Patent [19]

Teng et al.

[11] Patent Number: 4,722,834
[45] Date of Patent: Feb. 2, 1988

[54] METHOD OF USING 2-ALKOXY-N-(1-AZABICYCLO[2.2.2]OCT-3-YL)BENZAMIDE-N-OXIDES TO CONTROL EMESIS CAUSED BY ANTICANCER DRUGS

[75] Inventors: Lina C. Teng; Stephen C. Bearekman; Lennox B. Turnbull; Reevis S. Alphin; William L. Smith, all of Richmond, Va.

[73] Assignee: A. H. Robins Company, Incorporated, Richmond, Va.

[21] Appl. No.: 836,521

[22] Filed: Mar. 5, 1986

[51] Int. Cl.$^4$ .............................................. A61K 31/44
[52] U.S. Cl. ...................................... 424/10; 514/305
[58] Field of Search .......................... 514/305; 424/10

[56] References Cited

FOREIGN PATENT DOCUMENTS

99789A1  2/1984  European Pat. Off. ............ 514/305

Primary Examiner—Jerome D. Goldberg

[57] ABSTRACT

A method of controlling emesis caused by anticancer drugs with 2-alkoxy-N-(1-azabicyclo[2.2.2]oct-3-yl) benzamide-N-oxides having the formula:

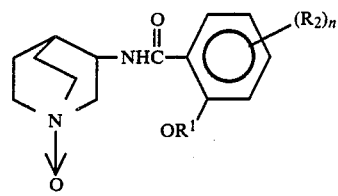

wherein $R_1$ is loweralkyl, and $R_2$ is selected from the group consisting of hydrogen, halo, 4,5-benzo, methylsulfonyl, loweralkoxy or Am and n is 1 or 2, and the pharmaceutically acceptable acid addition salts thereof is disclosed.

28 Claims, No Drawings

METHOD OF USING 2-ALKOXY-N-(1-AZABICYCLO[2.2.2]OCT-3-YL)BENZAMIDE-N-OXIDES TO CONTROL EMESIS CAUSED BY ANTICANCER DRUGS

BACKGROUND OF THE INVENTION

1. Field of Invention

The present invention relates to a method of controlling emesis caused by administration of anticancer drugs to warm blooded animals which utilizes certain N-(3-quinuclidinyl)benzamide-N-oxides; namely, the 2-alkoxy-N-(1-azabicyclo[2.2.2]oct-3-yl)benzamide-N-oxides.

2. Information Disclosure Statement

Certain compounds useful in the method of the present invention, namely 4-amino-N-(1-azabicyclo[2.2.2]oct-3-yl)-5-chloro-2-methoxybenzamide-N-oxide and N-(1-azabicyclo[2.2.2]oct-3-yl)-2-methoxybenzamide-N-oxide are disclosed in European Patent Application No. 0 099 789 A1 to be gastromotility agents; however, there is no disclosure of antiemetic properties.

Certain parent compounds useful in the preparation of N-oxide compounds used in the method of the present invention, namely 2-alkoxy-N-(1-azabicyclo[2.2.2]oct-3-yl) benzamides have been disclosed in U.S. patent application Ser. No. 597,275, filed Apr. 6, 1984, and a continuation U.S. patent application Ser. No. 788,190, filed Oct. 15, 1985, as having gastric emptying and antiemetic properties, especially antiemetic properties against emesis caused by administration of platinum-containing anticancer drugs.

Certain parent compounds useful in the preparation of N-oxide compounds used in the present invention, namely 2-alkoxy-N-(1-azabicyclo[2.2.2]oct-3-yl), have been disclosed in U.S. application for patent Ser. No. 836,518, filed Mar. 5, 1986 to alleviate emesis caused by non-platinum anticancer drugs.

SUMMARY OF THE INVENTION

The 2-alkoxy-N-(1-azabicyclo[2.2.2]oct-3-yl)benzamide-N-oxides of this invention have the formula:

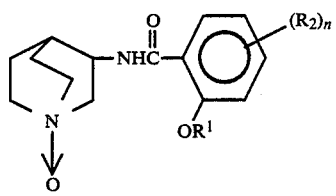

Formula I wherein $R_1$ is loweralkyl and $R_2$ is selected from the group consisting of hydrogen, halo, 4,5-benzo, methylsulfonyl, loweralkoxy or Am wherein Am is selected from amino, methylamino or dimethylamino, and n is 1 or 2, and the pharmaceutically acceptable acid addition salts thereof.

In the further definition of symbols in the formulas hereof and where they appear elsewhere throughout this specification and the claims, the terms have the following significance.

The term "loweralkyl" as used herein includes straight and branched chain radicals of up to eight carbons inclusive and is exemplified by such groups as methyl, ethyl, propyl, isopropyl, butyl, amyl, hexyl, heptyl, and octyl radicals and the like. The term "loweralkoxy" has the formula —O—loweralkyl.

The terms "halo", "halide", or "halogen" when referred to herein include fluorine, chlorine, bromine and iodine unless otherwise stated.

"Pharmaceutically acceptable acid addition salts" include the acid addition salts, hydrates, alcoholates and salts of the compounds of Formula I which are physiologically compatible in warm blooded animals. The acid addition salts may be formed by either strong or weak acids. Representative of strong acids are hydrochloric, sulfuric, and phosphoric acids. Representative of weak acids are fumaric, maleic, succinic, oxalic, citric, tartaric, cyclohexamic and the like.

Protected amino groups used in synthesis are acetylamino or benzoylamino radicals and the like on the benzamide moiety mentioned hereinbelow in synthetic methods.

Antiemetic properties in the control of emesis due to administration of anticancer drugs were determined by a modification of the method described by Gylys, J. A., et al. in Res. Chem. Pathol. Pharmacol. 23, No. 1, Jan. 1979, pp 61–68. Test results show that compounds of Formula I are effective in controlling emesis associated with the anticancer drug cisplatin (cis-diamminedichloroplatinum). Test procedures are explained and results given hereinbelow under Pharmacology. The compounds of Formula I can also be expected to control emesis caused by other anticancer drugs such as: cyclophosphamide (cytoxin), vincristine (leurocristine), procarbazine (N-(1-methylethyl)-4-[(2-methylhydrazino)methyl]benzamide), methotrexate, fluorouracil, mechlorethamine hydrochloride (2-chloro-N-(2-chloroethyl)-N-methylethanamine hydrochloride), doxorubicin (adriamycin), dactinomycin (antinomycin-D), and dacarbazine.

It is therefore a primary object to provide means for controlling violent emetic episodes due to the administration of anticancer drugs.

DETAILED DESCRIPTION OF THE INVENTION

Preparation of Benzamides

The N-oxide compounds of Formula I useful in the method of the invention are prepared by reacting a suitably activated benzoic acid derivative with 3-aminoquinuclidine to form the corresponding benzamide, followed by reaction with a peroxide, such as peracetic acid, perbenzoic acid, m-chloro-perbenzoic acid and hydrogen peroxide. Two general methods, A and B, are illustrated in the following equations:

Method A, using an Acid Chloride

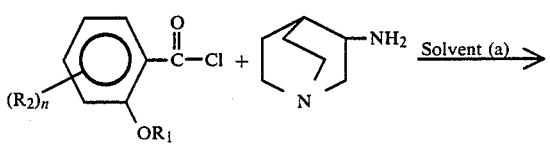

-continued
Method A, using an Acid Chloride

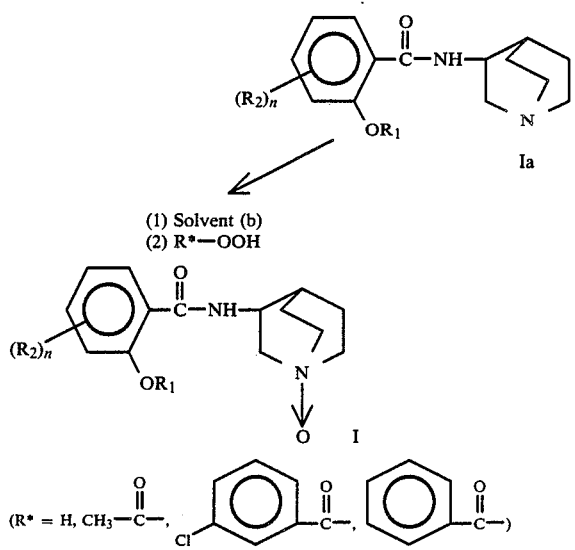

$R_1$, $R_2$ and n are as defined under Formula I except $R_2$ cannot be unprotected amino.
(a) Suitable solvents are chloroform, diethyl ether and tetrahydrofuran.
(b) Suitable solvent is methylene chloride/methanol [6:1].

Method B, using 1,1'-Carbonyldiimidazole

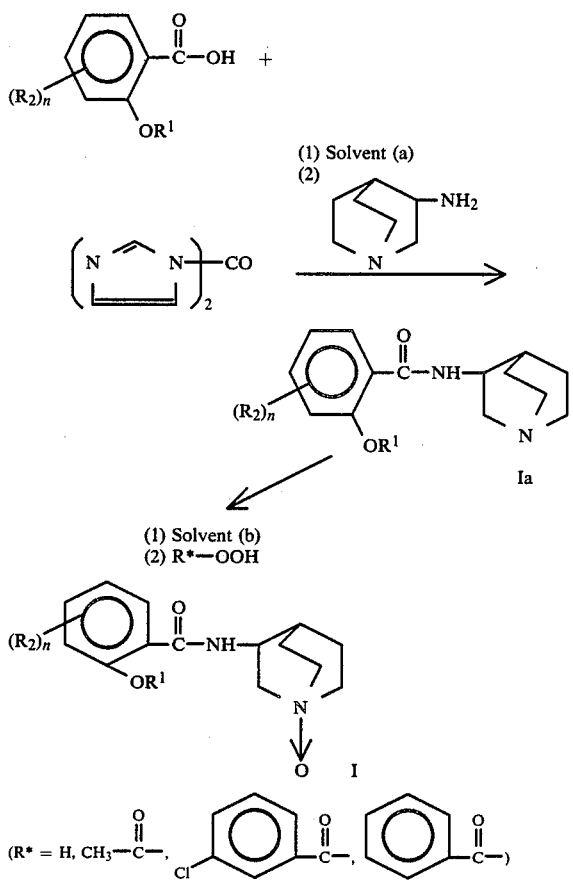

$R_1$, $R_2$ and n are as defined under Formula I.
(a) Suitable solvent is tetrahydrofuran.
(b) Suitable solvent is methylene chloride/methanol [6:1].

Compounds wherein $R_2$ is primary amino may also be prepared from a compound of Formula Ia prepared by Methods A or B, wherein $R_2$ is nitro by catalytic reduction of the nitro compound before the N-oxide is formed.

Alternatively, compounds wherein $R_2$ is amino may be prepared by procedures of Method A utilizing a starting benzoyl halide wherein the amino group has been protected, or they may be prepared from compounds of Formula Ia prepared in Methods A or B wherein $R_2$ is nitro and reducing the nitro radical to an amino radical, before the N-oxide is formed.

Preferably, the compounds wherein $R_2$ is amino or methylamino are prepared by Method B.

The free base of any compound of Formula I from its acid addition salt may be regenerated by usual procedures of partitioning between dilute aqueous base and a suitable solvent, separating the solvent layer, drying and evaporating.

A preferred group of compounds encompassed by Formula I have the formula:

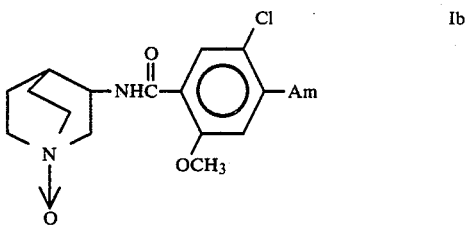

wherein Am is amino (i.e., —$NH_2$) or methylamino. The compounds are highly potent as antiemetics in conjunction with treatment of cancer with both platinum based anticancer drugs and non-platinum based anticancer drugs. As will be recognized from the above description, these compounds (Ib) are preferably prepared by Method B.

The following compound Preparations 1–13 and Examples 1–13 are provided merely by way of illustrating the methods of preparation and compounds and are not to be construed as being limiting in nature.

PREPARATION 1

N-(1-Azabicyclo[2.2.2]oct-3-yl)-5-chloro-2-methoxy-4-methylaminobenzamide, fumarate [1:1]

To a mixture of 1,1'-carbonyldiimidazole, 1.23 g (0.00756 mole) and 5-chloro-2-methoxy-4-methylaminobenzoic acid, 1.63 g (0.00756 mole) was added 50 ml of tetrahydrofuran. Nitrogen was bubbled into the solution for 30 minutes to remove any carbon dioxide that was present. To the solution was added 3-aminoquinuclidine, 0.95 g (0.00756 mole) in one portion, and the reaction mixture was stirred at ambient temperature for 16 hr. The reaction mixture was concentrated to an oil which was shown to be 1:1 mixture of the free base of the product and imidazole. The mixture was dissolved in 20 ml methanol and treated with a solution containing 0.47 g fumaric acid in 20 ml of hot methanol. Upon cooling, 1.52 g of white solid formed. Recrystallization from water-methanol gave 0.84 g of the product as a white solid, m.p. 237°–238° C.

Analysis: Calculated for $C_{20}H_{26}N_3O_6Cl$: C,54.61; H,5.96; N,9.55. Found: C,54.61; H,5.98; N,9.51.

PREPARATION 2

N-(1-Azabicyclo[2.2.2]oct-3-yl)-5-chloro-2-methoxy-4-(methylamino)benzamide, hydrochloride [1:1]

To an isopropyl alcohol solution of the free base of the title compound, such as was obtained by the procedure of Preparation 1, is added an equal molar amount of 37% (conc.) hydrochloric acid. The crude salt is separated by filtration and recrystallized from ethanol-water to give the title compound, m.p. 255°–258° C.

PREPARATION 3

4-Amino-N-(1-azabicyclo[2.2.2]oct-3-yl)-5-chloro-2-methoxybenzamide, fumarate [1:1]

In a closed system equipped with an oil bubbler, 30 ml of tetrahydrofuran was added to a mixture of 4-amino-5-chloro-2-methoxybenzoic acid, 2.02 g, (0.010 mole) and 1,1'-carbonyldiimidazole, 1.62 g (0.010 mole) with stirring. When evolution of carbon dioxide ceased, nitrogen was bubbled through the reaction mixture for 1 hr. A solution of 3-aminoquinuclidine, 1.26 g, (0.010 mole) in 10 ml tetrahydrofuran was added dropwise to the stirred reaction mixture and stirring at room temperature continued for 3 hrs. TLC analysis (3% conc. ammonium hydroxide solution in methanol) showed some product formation. The mixture was heated at reflux temperature for 18 hr and then concentrated to an oil. TLC analysis showed the presence of the product, imidazole, and 3-aminoquinuclidine. The oil was dissolved in methylene chloride (75 ml) and washed twice with 50 ml portions of aqueous sodium bicarbonate solution. The methylene chloride layer was dried over anhydrous magnesium sulfate and concentrated to yield 2.0 g (67%) of a glassy amorphous solid, the free base of the title compound.

In another reaction on a 0.020 mole scale, 5.18 g (83.8%) of the product as the free base was obtained.

The products were combined, dissolved in methanol (20 ml) and the solution was treated with a solution of fumaric acid (2.73 g) in methanol (50 ml). Absolute ether was added to precipitate the salt which was collected by filtration and recrystallized from methanol-water (200:20) with isopropyl ether added to the point of incipient cloudiness. The recrystallized salt (5.38 g) melted at 223°–225° C.

Analysis: Calculated for $C_{19}H_{24}N_3O_6Cl$: C,53.59; H,5.68; N,9.89. Found: C,53.35; H,5.72; N,9.95.

PREPARATION 4

4-Amino-N-(1-azabicyclo[2.2.2]oct-3-yl)-5-chloro-2-methoxybenzamide, hydrochloride, hydrate [1:1:1]

To an isopropyl alcohol solution of the free base of the title compound such as was obtained by the procedure of Preparation 3 is added an equal molar amount of 37% (conc.) hydrochloric acid. The crude salt is separated by filtration and recrystallized from acetone-water to give the title compound, m.p. 158°–160° C.

PREPARATION 5

N-(1-Azabicyclo[2.2.2]oct-3-yl)-2-methoxybenzamide, fumarate, hydrate [1:1:0.5]

In a closed system equipped with an oil bubbler, a solution of 2-methoxybenzoyl chloride, 2.76 g (0.0016 mole) in 50 ml absolute ether was added dropwise over 10 min to a stirred solution of 3-aminoquinuclidine, 1.81 g (0.0144 mole) in 100 ml absolute ether. After the addition was completed, the mixture was stirred at room temperature for an additional 2 hr. The solid hydrochloride salt was collected by filtration under nitrogen. The salt (3.83 g) was dissolved in sodium bicarbonate solution and extracted twice with 25 ml portions of methylene chloride. The extract was dried over magnesium sulfate and concentrated to yield 1.25 g clear oil (33.3%). TLC analysis (3% conc. ammonium hydroxide in methanol) showed the free base to be pure. A solution of 1.17 g of the free base in 5 ml methanol was treated with a solution of 0.52 g fumaric acid in 10 ml methanol. Isopropyl ether was added to give approximately 100 ml of solution from which the fumarate salt precipitated. The salt was collected under nitrogen and dried in a vacuum oven at 60° C. Overnight. NMR and elemental analyses showed that the product was a hemihydrate.

Analysis: Calculated for $C_{19}H_{25}N_2O_{6.5}$: C,59.21; H,6.54; N,7.27. Found: C,59.18; H,6.30; N,7.25.

PREPARATION 6

N-(1-Azabicyclo[2.2.2]oct-3-yl)-2,4-dimethoxybenzamide, hydrochloride [1:1]

A mixture of 3-aminoquinuclidine dihydrochloride, 6.95 g, (0.349), 2,4-dimethoxybenzoyl chloride, 700 g, (0.0349 mole), anhydrous sodium carbonate, 36.99 g, (0.349 mole), 175 ml water, and 175 ml chloroform was stirred rapidly to achieve good mixing of the 2 layers for 20 hrs. The chloroform layer was then separated, washed with water, dried over anhydrous magnesium sulfate, and concentrated to an impure oil. The oil was triturated twice with 20 ml portions of petroleum ether to remove some impurities. The oil was then dissolved in diethyl ether and filtered to remove a small amount of insoluble material. The filtrate was treated with ethereal hydrogen chloride and the resulting salt collected to yield 2.70 g (23.7% yield) white solid. The salt was recrystallized from ethanol-isopropyl ether. Further recrystallization from methanol-ethyl ether yielded a white solid, m.p. 211°–212° C. The NMR analysis was satisfactory.

Analysis: Calculated for $C_{16}H_{23}N_2O_3Cl$: C,58.80; H,7.09; N,8.57. Found: C,58.38; H,7.13; N,8.44.

PREPARATION 7

N-(1-Azabicyclo[2.2.2]oct-3-yl)-2,4-dimethoxybenzamide, sulfate [1:1]

In a closed system equipped with an oil bubbler, a solution of 2,4-dimethoxybenzoyl chloride, 13.08 g, (0.0652 mole) in 200 ml absolute ether was dded dropwise over 30 minutes to a stirred solution of 3-aminoquinuclidine, 7.80 g, (0.0619 mole) in 200 ml absolute ether. The mixture was stirred overnight, and the solid hydrochloride salt of the product was filtered under nitrogen. The material was dried in a vacuum oven at 40° C. to give 18.70 g (92%). A 2.94 g (0.009 mole) portion of the hydrochloride salt in 20 ml methanol was treated with a solution of sodium methoxide prepared from 0.23 g (0.010 mole) sodium metal and 10 ml methanol. After standing a few minutes, the mixture was filtered and the filtrate concentrated on a rotary evaporator, and the residue was triturated with 75 ml methylene chloride. After filtering to remove some insoluble solids, the filtrate was concentrated to yield 2.53 g of the free base of the title compound (97% recovery from the hydrochloride salt). The free base was dissolved in 100 ml acetone and concentrated sulfuric acid (0.483 ml) added dropwise with stirring. The solid that formed was collected under nitrogen to give 2.76 g of the salt which recrystallized from methanol-isopropyl ether and dried in a vacuum oven at 60° C. for 2 hr and then overnight at 78° C., m.p. 223°-225° C.

Analysis: Calculated for $C_{16}H_{24}N_2O_7S$: C,49.47; H,6.23; N,7.23. Found: C,49.41; H,6.30; N,7.25.

PREPARATION 8

N-(1-Azabicyclo[2.2.2]oct-3-yl)-2,4-dimethoxybenzamide, fumarate [1:1.5]

In a closed system equipped with an oil bubbler, tetrahydrofuran, 100 ml, was added to a mixture of 2,4-dimethoxybenzoic acid, 3.64 g (0.020 mole) and 1,1'carbonyldimidazole, 3.24 g (0.020 mole). No evolution of carbon dioxide was observed and after stirring for 3 hrs, TLC (ethyl acetate) and mass spectral analysis showed that the starting material had reacted to form (2,4-dimethoxybenzoyl) imidazole and imidazole. A solution of 3-aminoquinuclidine, 2.52 g (0.020 mole) in 10 ml tetrahydrofuran was added to the mixture, and the solution was heated to reflux temperature for 1 hr and then allowed to stand overnight at room temperature. A solution of fumaric acid, 2.32 g (0.020 mole) in 50 ml methanol was added to the reaction mixture. Tetrahydrofuran was added until the solution became slightly turbid. The solution was chilled in a refrigerator. The solid which precipitated from solution was collected by filtration and found to be a fumarate salt of 3-aminoquinuclidine. The filtrate was concentrated to an oil and triturated with tetrahydrofuran. The solid precipitate which formed on standing was filtered and shown by TLC (3% concentrated ammonium hydroxide in methanol) to be the desired product plus traces of imidazole and 3-aminoquinuclidine. Recrystallization from methanol-iropropyl ether gave 5.41 g white crystalline solid (67% yield calculated as the monofumarate). NMR and elemental analysis showed the salt to contain less than one equivalent of fumaric acid. The salt was dissolved in boiling methanol (50 ml) and treated with an additional 0.77 g (0.0066 mole) fumaric acid in 10 ml hot methanol. Isopropyl ether was added until the hot solution became turbid. The solid obtained on cooling was collected, recrystallized from methanol-isopropyl ether and dried in a vacuum oven at 78° C. overnight. NMR and elemental analysis showed the salt to be a 1.5 fumarate, m.p. 192°-192.5° C.

Analysis: Calculated for $C_{22}H_{28}N_2O_9$: C,56.89; H,6.08; N,6.03. Found: C,56.81; H,6.13; N,6.04.

PREPARATION 9

N-(1-Azabicyclo[2.2.2]oct-3-yl)-2-propoxybenzamide, hydrochloride [1:1]

To a solution of 3.82 g (0.0192 mole) of 3-amino quinuclidine dihydrochloride in about 25 ml of carbon dioxide-free water was added 8 g (0.025 mole) of barium hydroxide octahydrate. The mixture was warmed for 5 minutes and then dried to a powder on a rotary evaporator. While protecting from contamination with carbon dioxide in the atmosphere, the powder was extracted in sequence with hot benzene and a 1:1 mixture of benzene-methylene chloride solution. The combined extracts were dried over magnesium sulfate and the mixture filtered. To the filtrate with agitation was added dropwise a solution of 3.4 g (0.0171 mole) of 2-propoxybenzoyl chloride in 50 ml of methylene chloride. The mixture was warmed on a steam bath to evaporate about 75% of the methylene chloride. Ligroin (60-110) was added and the mixture solidified. The solid was recrystallized from anhydrous ethyl alcohol to give 3.9 g (62.0%), m.p. 210°-211° C.

Analysis: Calculated for $C_{17}H_{25}N_2O_2Cl$: C,62.86: H7.75; N,8.62. Found: C,62.62; H,7.59; N,8.54.

PREPARATION 10

N-(1-Azabicyclo[2.2.2]oct-3-yl)-3-methoxy-2-naphthalenecarboxamide, hydrochloride [1:1]

A solution of 1.69 g (0.00768 mole) of 3-methoxy-2-naphthc acid chloride in 15 ml of methylene chloride was added dropwise to a stirred solution of 0.97 g (0.00768 mole) of 3-aminoquinuclidine in 25 ml of methylene chloride in a closed system equipped with an oil bubbler. The reaction mixture was stirred overnight at ambient temperature, and then concentrated to give an off-white glassy solid. Two recrystallizations from methanol-isopropyl ether gave 1.95 g (73.4%) of the product as an off-white solid which was vacuum dried at ambient temperature, m.p. 248°-252° C.

Analysis: Calculated for $C_{19}H_{23}N_2O_2Cl$: C,65.79; H,6.68; N,8.08. Found: C,65.40; H,6.72; N,8.01.

PREPARATION 11

N-(1-Azabicyclo[2.2.2]oct-3-yl)-5-chloro-4-dimethylamino-2-methoxybenzamide, fumarate Using the procedure of Preparation 1, and substituting 5-chloro-4-dimethylamino-2-methoxybenzoic acid for 5-chloro-2-methoxy-4-methylaminobenzoic acid, there is obtained the title compound.

PREPARATION 12

N-(1-Azabicyclo[2.2.2]oct-3-yl)-2-methoxy-5-(methylsulfonyl) benzamide, hydrochloride [1:1]

A solution of 3-aminoquinuclidine (1.50 g, 0.0119 mole) in 20 ml tetrahydrofuran was added dropwise to a stirred solution of 2-methoxy-5-methanesulfonylbenzoyl chloride (2.95 g, 0.0119 mole) in 100 ml tetrahydrofuran. The mixture was stirred at ambient temperature for 20 hr, and filtered to yield 4.00 g (89.7%) of the product as the hydrochloride salt. The material was heated in 100 ml of boiling absolute ethanol and 50 ml methanol was added to give a clear solution. The solution was evaporated to a volume of 100 ml and cooled. The precipitate which formed was collected by filtration and vacuum dried at 110° C. for 8 hr, m.p. 219°-221° C.

Analysis: Calculated for $C_{16}H_{23}N_2O_4SCl$: C,51.26; H,6.18; N,7.47. Found: C,51.19; H,6.26; N,7.35.

PREPARATION 13

N-(1-Azabicyclo[2.2.2]oct-3-yl)-5-bromo-2,4-dimethoxybenzamide, hydrochloride [1:1]

A solution of 3-aminoquinuclidine (1.12 g, 0.0089 mole) in 20 ml tetrahydrofuran was added dropwise to a stirred solution of 5-bromo-2,4-dimethoxybenzoyl chloride (2.50 g, 0.0089 mole) in 100 ml tetrahydrofuran. The mixture was stirred at ambient temperature for 65 hr, and the solid was collected by filtration to yield 2.77 g. Recrystallization from methanol-isopropyl ether gave 1.45 g (40.2%), m.p. 240°-243° C.

Analysis: Calculated for $C_{16}H_{21}N_2O_3Br \cdot HCl$: C,47.37; H,5.47; N,6.90. Found: C,47.23; H,5.62; N,6.85.

EXAMPLE 1

N-(1-Azabicyclo[2.2.2]oct-3-yl)-5-chloro-2-methoxy-4-methylaminobenzamide-N-oxide, hydrochloride [1:1]

A solution of 40.0 g of N-(1-azabicyclo[2.2.2]oct-3-yl)-5-chloro-2-methoxy-4-methylaminobenzamide, hydrochloride [1:1] in 300 ml of water was treated with 5.7 ml of 50% sodium hydroxide solution and the precipitate was collected, rinsed with water and dried to give 35.2 g of white granules. This solid was dissolved in methylene chloride (150 ml) and methanol (25 ml) and treated with 23.3 g of 35% peracetic acid. After ½ hr stirring, the solution was concentrated under reduced pressure at 70° C. for 2 hr. The residue was triturated with isopropanol (hot). The slurry was cooled and the precipitate collected and dried to give 39.7 g of light yellow crystalline powder. This acetic acid salt of the desired product (by NMR) was converted to the hydrochloric acid salt by slurrying it in absolute ethanol and adding one equivalent of hydrogen chloride in isopropanol. This gave a yellow solution which on cooling deposited fine, pale yellow crystals. The crystals were collected and recrystallized from 150 ml of absolute ethanol and 75 ml of 95% ethanol to give, after drying at high vacuum and 75° C. for 68 hr, 16 g (38%) of a pale yellow powder, m.p. 232°–235° C. (with decomposition).

Analysis: Calculated for $C_{10}H_{22}N_3O_3Cl.HCl$: C,51.07; H,6.16; N,11.17. Found: C,50.57; H,6.19; N,10.95.

EXAMPLE 2

N-(1-Azabicyclo[2.2.2]oct-3-yl)-5-chloro-2-methoxy-4-methylaminobenzamide-N-oxide, hydrochloride N-(1-Azabicyclo[2.2.2]oct-3-yl)-5-chloro-2-methoxy-4-methylaminobenzamide, fumarate [1:1] is converted to the free base by partitioning with aqueous sodium hydroxide and methylene chloride. Using the procedure of Example 1, the free base is reacted with peracetic acid to obtain the N-oxide and finally with hydrogen chloride in isopropanol to give the hydrochloride.

EXAMPLE 3

4-Amino-N-(1-azabicyclo[2.2.2]oct-3-yl)-5-chloro-2-methoxybenzamide-N-oxide, hydrochloride [1:1]

This compound was prepared by the procedure used to synthasize the compound of Example 1. A batch of 40 g 4-amino-N-(1-azabicyclo[2.2.2]oct-3-yl)-5-chloro-2-methoxybenzamide, hydrochloride, hydrate [1:1:1] was treated with sodium hydroxide, then with one equivalent of 35% peracetic acid and finally with hydrogen chloride in isopropanol to give crude title compound which was then recrystallized from 95% ethanol to give 20 g (48%) of title compound as a pale yellow crystalline solid, m.p. 240°–242° C. (with decomposition).

Analysis: Calculated for $C_{15}H_{20}N_3O_3Cl.HCl$: C,49.74; H,5.84; N,11.60. Found: C,49.52; H,5.92; N,11.52.

EXAMPLE 4

4-Amino-N-(1-azabicyclo[2.2.2]oct-3-yl)-5-chloro-2-methoxybenzamide-N-oxide, hydrochloride 4-Amino-N-(1-azabicyclo[2.2.2]oct-3-yl)-5-chloro-2-methoxybenzamide fumarate [1:1] is converted to the free base by partitioning with aqueous sodium hydroxide and methylene chloride. Using the procedure of Example 1, the free base is reacted with peracetic acid to obtain the N-oxide and finally with hydrogen chloride in isopropanol to give the hydrochloride.

EXAMPLE 5

N-(1-Azabicyclo[2.2.2]oct-3-yl)-2-methoxybenzamide-N-oxide, hydrochloride

N-(1-Azabicyclo[2.2.2]oct-3-yl)-2-methoxybenzamide, fumarate, hydrate [1:1:0.5] is converted to the free base by partitioning with aqueous sodium hydroxide and methylene chloride. Using the procedure of Example 1, the free base is reacted with peracetic acid to obtain the N-oxide and finally with hydrogen chloride in isopropanol to give the hydrochloride.

EXAMPLE 6

N-(1-Azabicyclo[2.2.2]oct-3-yl)-2,4-dimethoxybenzamide-N-oxide, hydrochloride

N-(1-Azabicyclo[2.2.2]oct-3-yl)-2,4-dimethoxybenzamide, hydrochloride [1:1] is converted to the free base by partitioning with aqueous sodium hydroxide and methylene chloride. Using the procedure of Example 1, the free base is reacted with peracetic acid to obtain the N-oxide and finally with hydrogen chloride in isopropanol to give the hydrochloride.

EXAMPLE 7

N-(1-Azabicyclo[2.2.2]oct-3-yl)-2,4-dimethoxybenzamide-N-oxide, hydrochloride

N-(1-Azabicyclo[2.2.2]oct-3 yl)-2,4-dimethoxybenzamide, sulfate [1:1] is converted to the free base by partitioning with aqueous sodium hydroxide and methylene chloride. Using the procedure of Example 1, the free base is reacted with peracetic acid to obtain the N-oxide and finally with hydrogen chloride in isopropanol to give the hydrochloride.

EXAMPLE 8

N-(1-Azabicyclo[2.2.2]oct-3-yl)-2,4-dimethoxybenzamide-N-oxide, hydrochloride

N-(1-Azabicyclo[2.2.2]oct-3-yl)-2,4-dimethoxybenzamide, fumarate [1:1.5] is converted to the free base by partitioning with aqueous sodium hydroxide and methylene chloride. Using the procedure of Example 1, the free base is reacted with peracetic acid to obtain the N-oxide and finally with hydrogen chloride in isopropanol to give the hydrochloride.

EXAMPLE 9

N-(1-Azabicyclo[2.2.2]oct-3-yl)-2-propoxybenzamide-N-oxide, hydrochloride

N-(1-Azabicyclo[2.2.2]oct-3-yl)-2-propoxybenzamide hydrochloride [1:1] is converted to the free base by partitioning with aqueous sodium hydroxide and methylene chloride. Using the procedure of Example 1, the free base is reacted with peracetic acid to obtain the N-oxide and finally with hydrogen chloride in isopropanol to give the hydrochloride.

EXAMPLE 10

N-(1-Azabicyclo[2.2.2]oct-3-yl)-3-methoxy-2-naphthalenecarboxamide-N-oxide, hydrochloride N-(1-Azabicyclo[2.2.2]oct-3-yl)-3-methoxy-2-naphthalenecarboxamide, hydrochloride [1:1] is converted to the free base by partitioning with aqueous sodium hydroxide and methylene chloride. Using the procedure of Example 1, the free base is reacted with peracetic acid to obtain the N-oxide and finally is reacted with hydrogen chloride in isopropanol to give the hydrochloride.

EXAMPLE 11

N-(1-Azabixyclo[2.2.2]oct-3-yl)-5-chloro-4-dimethylamino-2-methoxybenzamide-N-oxide, hydrochloride N-(1-Azabicyclo[2.2.2]oct-3-yl)-5-chloro-4-dimethylamino-2-methoxybenzamide, furmarate is converted to the free base by partitioning with aqueous sodium hydroxide and methylene chloride. Using the procedure of Example 1, the free base is reacted with peracetic acid to obtain the N-oxide and finally with hydrogen chloride in isopropanol to give the hydrochloride.

EXAMPLE 12

N-(1-Azabicyclo[2.2.2]oct-3-yl)-2-methoxy-5-(methylsulfonyl)benzamide-N-oxide, hydrochloride N-(1-Azabicyclo[2.2.2]oct-3-yl)-2-methoxy-5-(methylsulfonyl)benzamide, hydrochloride [1:1] is converted to the free base by partitioning with aqueous sodium hydroxide and methylene chloride. Using the procedure of Example 1, the free base is reacted with peracetic acid to obtain the N-oxide and finally with hydrogen chloride in isopropanol to give the hydrochloride.

EXAMPLE 13

N-(1-Azabicyclo[2.2.2]oct-3-yl)-5-bromo-2,4-dimethoxy-benzamide-N-oxide, hydrochloride N-(1-Azabicyclo[2.2.2]oct-3-yl)-5-bromo-2,4-dimethoxy-benzamide, hydrochloride [1:1] is converted to the free base by partitioning with aqueous sodium hydroxide and methylene chloride. Using the procedure of Example 1, the free base is reacted with peracetic acid to obtain the N-oxide and finally with hydrogen chloride in isopropanol to give the hydrochloride.

PHARMACOLOGY

The action of compounds of this invention in controlling emesis caused by administration of platinum-based anticancer drugs is demonstrated by the following procedure:

TEST ON EMESIS CAUSED BY CISPLATIN (cis-diammine-dichloro-platinum)

As stated hereinabove, the procedure used to test compounds of the present invention for antiemetic properties is a modification of the method of Gylys, et al. Adult, mongrel, unfasted dogs of both sexes were randomly assigned into treatment groups, with each treatment group consisting of four dogs. On the dosing day all dogs were given cisplatin, 3.0 mg/kg, intravenously. Sixty minutes later, the dogs in the control treatment group were given deionized water 0.1 ml/kg intravenously, the dogs in the test group were given the compound of example 3, at a dose of 1.0 mg/kg intravenously. All doses were administered as a solution by means of a syringe and needle, and each dog's emetic episodes were recorded for 5 hr after the administration of cisplatin. Test results show that the compound of Example 3 inhibited 100% of the emetic episodes in dogs when compared to the number of emetic episodes exhibited by dogs receiving the control (deionized water).

When the following anticancer drugs, mechlorethamine hydrochloride, doxorubicin, dactinomycin, or dacarbazine are substituted for cisplatin in the foregoing test procedure, efficacy in controlling emesis with compounds of Formula I is expectable and is intended to be indicative of the general utility of the compounds in controlling emesis caused by non-platinum based anticancer drugs. Examples of additional non-platinum drugs for which Formula I compounds are anticipated to be effective are: cytoxin, leurocristine, procarbazine, methotrexate and fluorouracil.

PHARMACEUTICAL METHODS AND COMPOSITIONS

Generally, the method of controlling emesis associated with anticancer drugs in accordance with this invention comprises administering internally to warm blooded animals including human beings certain 2-alkoxy-N-(1-azabicyclo [2.2.2]oct-3-yl)benzamide-N-oxides of Formula I, preferably Formula Ib, or a non-toxic organic or inorganic acid addition salt thereof in a wide variety of pharmaceutical forms well known in the art, preferably with a non-toxic pharmaceutical carrier such as is described below in an amount to control emesis associated with anticancer drugs. The active agent is administered orally, subcutaneously, intravenously or intramuscularly or parenterally and, if necessary, in repeated doses until satisfactory response is obtained. The daily dosage is from about 5 to about 300 mg of active medication, advantageously from about 5 mg to 50 mg. Co-administration of the compounds of Formula I and anticancer drugs is within the purview of the method of this invention.

In any particular method of controlling emesis due to administration of anticancer drugs in cancer treatment, it may at times be desirable to administer a mixture comprised of compounds of Formula I, preferably Ib, and anticancer drugs to the animal, including humans, the daily dosage being within the range cited above.

The pharmaceutical compositions, useful as antiemetics against emesis caused by anticancer drugs, of this invention comprise at least one of the compounds of Formula I, preferably Ib above, as active ingredients in an amount to provide effective antiemetic action against emesis caused by anticancer drugs. The compositions contain 0.05 to 100 mg active medicament per unit dose. Preferably, compositions contain from about 5 mg to 100 mg of medicament, advantageously from about 5 mg to about 50 mg per unit dose. The compounds are thus presented in a therapeutic composition suitable for oral, parenteral, subcutaneous, intramuscular, intraperitoneal or intravenous administration. Thus, for example, compositions for oral administration can take the form of elixirs, capsules, tablest or coated tablets containing carriers conveniently used in the pharmaceutical art. Exemplary of solid carriers including tableting and capsulating excipients are lactose, sucrose, potato and maize starches, talc, gelatin, agar, pectin or acacia, stearic and silicic acids, magnesium stearate, terra alba and polyvinyl pyrrolidone.

For parenteral administration, the carrier or excipient can be comprised of a sterile parenterally acceptable liquid, e.g., water or arachis oil contained in ampoules.

The pharmaceutical compositions for use in conjunction with administration of anticancer drugs in cancer treatment will be formulated to contain from about 0.1 mg/kg to about 3.0 mg/kg body weight, preferably 1.0 mg/kg body weight or less of a compound of Formula I. As stated above, co-formulation of anticancer drugs and compounds of Formula I are within the scope of this invention and it is only necessary that the active ingredient of Formula I constitute an effective amount.

In all of the above, it is only necessary that a suitable effective dosage will be consistent with the dosage form employed. The exact individual dosages, as well as daily dosages, will of course be determined according to standard medical principles under the direction of a physician or veterinarian.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention, and it is therefore understood that the invention is to be limited only by the scope of the appended claims.

What is claimed is:

1. A method for treating warm blooded animals for emesis caused by administration of anticancer drugs during cancer treatment which comprises internally administering to said animals an emesis-inhibiting effective amount of a compound selected from the group consisting of 2-alkoxy-N-(1-azabicyclo[2.2.2]oct-3-yl) benzamide-N-oxides of the formula:

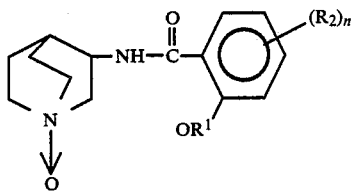

wherein;
$R_1$ is loweralkyl containing up to eight carbons,
$R_2$ is selected from the group consisting of hydrogen, halo, 4,5-benzo, methylsulfonyl, loweralkoxy containing up to eight carbons or Am wherein Am is selected from amino, methylamino or dimethylamino,
n is 1 or 2,
and the pharmaceutically acceptable acid addition salts thereof.

2. The method of claim 1 wherein the compound is N-(1-azabicyclo[2.2.2]oct-3-yl)-5-chloro-2-methoxy-4-methylaminobenzamide-N-oxide or a pharmaceutically acceptable salt thereof.

3. The method of claim 1 wherein the compound is N-(1-azabicyclo[2.2.2]oct-3-yl)-5-chloro-2-methoxy-4-methylaminobenzamide-N-oxide, hydrochloride [1:1].

4. The method of claim 1 wherein the compound is 4-amino-N-(1-azabicyclo[2.2.2]oct-3-yl)-5-chloro-2-methoxybenzamide-N-oxide or a pharmaceutically acceptable salt thereof.

5. The method of claim 1 wherein the compound is 4-amino-N-(1-azabicyclo[2.2.2]oct-3-yl)-5-chloro-2-methoxybenzamide-N-oxide, hydrochloride [1:1].

6. The method of claim 1 wherein the compound is N-(1-azabicyclo[2.2.2]oct-3-yl)-2-methoxybenzamide-N-oxide or a pharmaceutically acceptable salt thereof.

7. The method of claim 1 wherein the compound is N-(1-azabicyclo[2.2.2]oct-3-yl)-2,4-dimethoxybenzamide-N-oxide or a pharmaceutically acceptable salt thereof.

8. The method of claim 1 wherein the compound is N-(1-azabicyclo[2.2.2]oct-3-yl)-2-propoxybenzamide-N-oxide or a pharmaceutically acceptable salt thereof.

9. The method of claim 1 wherein the compound is N-(1-azabicyclo[2.2.2]oct-3-yl)-3-methoxy-2-naphthalenecarboxamide-N-oxide or a pharmaceutically acceptable salt thereof.

10. The method of claim 1 wherein the compound is 1-(azabicyclo[2.2.2]oct-3-yl)-5-chloro-4-dimethylamino-2-methoxybenzamide-N-oxide or a pharmaceutically acceptable salt thereof.

11. The method of claim 1 wherein the compound is N-(1-azabicyclo[2.2.2]oct-3-yl)-2-methoxy-5-(methylsulfonyl)-benzamide-N-oxide or a pharmaceutically acceptable salt thereof.

12. The method of claim 1 wherein the compound is N-(1-azabicyclo[2.2.2]oct-3-yl)-5-bromo-2,4-dimethoxybenzamide-N-oxide or a pharmaceutically acceptable salt thereof.

13. The method of claim 1 wherein said anticancer drug causing emesis is cis-diammine-dichloro-platinum.

14. The method of claim 1 wherein said anticancer drug causing emesis is mechlorethamine hydrochloride.

15. The method of claim 1 wherein said anticancer drug causing emesis is doxorubicin.

16. The method of claim 1 wherein said anticancer drug causing emesis is dactinomycin.

17. The method of claim 1 wherein said anticancer drug causing emesis is dacarbazine.

18. A method for treating warm blooded animals for emesis caused by administration of anticancer drugs during cancer treatment which comprises administering to said animals an emesis inhibiting effective amount of a compound selected from the group consisting of 4-amino-(1-azabicyclo[2.2.2]oct-3-yl)-5-chloro-2-methoxybenzamide-N-oxides of the formula:

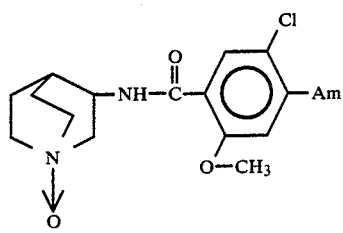

wherein;
Am is selected from amino, methylamino or dimethylamino,
and the pharmaceutically acceptable salts thereof.

19. The method of claim 18 wherein the compound is N-(1-azabicyclo[2.2.2]oct-3-yl)-5-chloro-2-methoxy-4-methylaminobenzamide-N-oxide or a pharmaceutically acceptable salt thereof.

20. The method of claim 18 wherein the compound is N-(1-azabicyclo[2.2.2]oct-3-yl)-5-chloro-2-methoxy-4-methylaminobenzamide-N-oxide, hydrochloride [1:1].

21. The method of claim 18 wherein the compound is 4-amino-N-(1-azabicyclo[2.2.2]oct-3-yl)-5-chloro-2-methoxybenzamide-N-oxide or a pharmaceutically acceptable salt thereof.

22. The method of claim 18 wherein the compound is 4-amino-N-(1-azabicyclo[2.2.2]oct-3-yl)-5-chloro-2-methoxybenzamide-N-oxide, hydrochloride [1:1].

23. The method of claim 18 wherein the compound is N-(1-azabicyclo[2.2.2]oct-3-yl)-5-chloro-2-methoxy-4-dimethylaminobenzamide-N-oxide or a pharmaceutically acceptable salt thereof.

24. The method of claim 18 wherein said anticancer drug causing emesis is cis-diammine-dichloro-platinum.

25. The method of claim 18 wherein said anticancer drug causing emesis is mechlorethamine hydrochloride.

26. The method of claim 18 wherein said anticancer drug causing emesis is doxorubicin.

27. The method of claim 18 wherein said anticancer drug causing emesis is dactinomycin.

28. The method of claim 18 wherein said anticancer drug causing emesis is dacarbazine.

* * * * *